United States Patent [19]

Ogawa et al.

[11] Patent Number: 4,491,594

[45] Date of Patent: Jan. 1, 1985

[54] METHOD FOR TREATMENT OF SEIZURES

[75] Inventors: Norio Ogawa; Shuji Tsukamoto, both of Okayama, Japan

[73] Assignee: Eisai Co., Ltd., Tokyo, Japan

[21] Appl. No.: 585,805

[22] Filed: Mar. 2, 1984

[30] Foreign Application Priority Data

Mar. 8, 1983 [JP] Japan ................... 58-36568

[51] Int. Cl.$^3$ .................... A61K 31/12; A61K 37/48
[52] U.S. Cl. ........................ 424/331; 424/94
[58] Field of Search ................ 424/331, 94

[56] References Cited

U.S. PATENT DOCUMENTS

| 4,068,001 | 1/1978 | Kanno ............... 424/331 |
| 4,068,003 | 1/1978 | Miyata .............. 424/331 |
| 4,073,883 | 2/1978 | Yasuda et al. ....... 424/331 |

Primary Examiner—Stanley J. Friedman
Attorney, Agent, or Firm—Flynn, Thiel, Boutell & Tanis

[57] ABSTRACT

A remedial and prophylactic agent for seizures is disclosed which contains, as an active ingredient, coenzyme Q represented by the general formula:

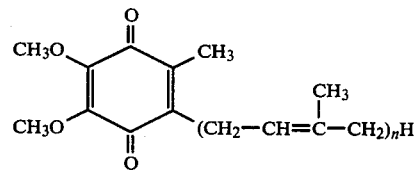

wherein n is an integer of 7 to 10.

5 Claims, 6 Drawing Figures

METHOD FOR TREATMENT OF SEIZURES

This invention relates to a remedial and prophylactic agent for the treatment of seizures. More particularly, it relates to a composition for treatment of seizures which contains, as an active ingredient, coenzyme Q represented by the following general formula:

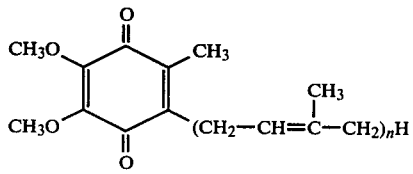

wherein n is an integer of from 7 to 10. The present invention further relates to a method of treatment of seizures employing such a composition.

Coenzyme(s) Q, also called ubiquinones, were discovered in the lipid of bovine heart mitochondria by Crane of the University of Wisconsin in 1957. Naturally occurring forms of coenzyme Q have different values of "n" in the above general formula.

The action of coenzyme Q in the living body is not yet definitely known, but it is generally considered that this type of coenzyme participates in the electron transfer system in mitochondria. It is also believed that coenzyme Q activates cellular respiration and, in conjunction therewith, promotes the production of ATP, thus playing an important role in activating various tissues of the living body. Many studies have been made on medical applications of coenzyme Q, and at present, use of coenzyme $Q_{10}$ (n=10 in the general formula above) as a remedial agent for congestive heart failure is known.

SUMMARY OF THE INVENTION

Assiduous studies by the present inventors on medical applications of coenzymes Q have led to the unexpected finding that coenzymes Q are effective for the treatment and prevention of spasms. This finding led to the attainment of the present invention.

The term "seizure" used in the context of this description of the invention refers generically to sudden and involuntary contractions of muscles over the whole or part of the body, which contractions are caused by an abnormal excitation of the central nervous system. A typical example of such spasms is the spasms that occur due to epilepsy.

DETAILED DESCRIPTION OF THE INVENTION

The coenzymes Q used in this invention can be produced by any applicable method, such as by synthesis or fermentation. Coenzyme $Q_{10}$, which is effective for use in this invention, is a yellow or orange powder which is soluble in chloroform, benzene, carbon tetrachloride, acetone and ether, but insoluble in ethanol, water and methanol. Its melting point is about 48° C.

The effects of the present invention are demonstrated by the experimental examples given below.

EXPERIMENTAL EXAMPLE 1

(1) Method (a) Animals used

Male Sprague-Dawley rats each having a body weight in the range of 250 to 350 g were used for the experiment.

(b) Method of forming penicillin focus

Each test rat, anesthetized with ether and immobilized with succinylcholine was subjected to tracheal intubation and fixed to a stereotaxic instrument under artificial respiration. A hole about 3 mm in diameter was made at a part of the skull corresponding to the left-side sensory-motor cortex and the dura mater was cut out to expose the cerebral cortex surface. The skull was immersed in a physiological saline solution. A 2 mm square filter paper impregnated with 85 U/$\mu$l of penicillin (penicillin G) was then applied directly to the cerebral surface to form a penicillin cortical focus. This focus is a typical epilepsy model.

(c) Electroencephalographic recording

Each rat skull was bared and screw electrodes, four in all, were fixedly planted at the following four locations: two sites 2 mm to the left and right, respectively, from a position 2 mm forward of the bregma, and two sites 3 mm to the left and right, respectively, from a position 6 mm rearward of the bregma. Unipolar and bipolar electroencephalograms (EEG) were recorded by the electrodes. Electrocardiogram readings were simultaneously taken. EEG lead measurements were conducted of (1) four bipolar leads comprising a lead from the left sincipital region to the left occipital region, a lead from the right sincipital region to the right occipital region, a lead from the left to the right sincipital region, and a lead from the left to the right occipital region, and (2) four unipolar leads comprising leads from each of the left sincipital region, left occipital region, right sincipital region and right occipital region.

Figure 6:
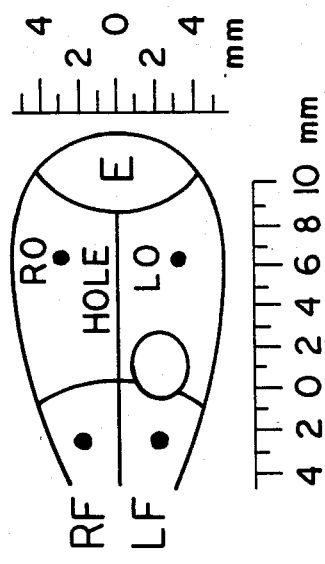
FIG. 6 indicates a corticogram used in Experimental Example 1.

The corticogram shown in FIG. 6 illustrates the procedure employed. The recordings were carried out from 4 epidural electrodes. LF-LO: bipolar recording from left frontal electrode (LF) to left occipital electrode (LO), RF-RO: bipolar recording from right frontal electrode (RF) to right occipital electrode (RO), LF-RF: bipolar recording from LF to RF, LO-RO: bipolar recording from LO to RO, LF-E: unipolar recording from LF, LO-E: unipolar recording from LO, RF-E: unipolar recording from RF, RO-E: unipolar recording from RO.

(d) Medication 83.5 U/$\mu$l of penicillin G was absorbed into a 2 mm square filter paper and directly applied to the cerebral cortex surface from an opening formed around the left sensory-motor cortex. coenzyme $Q_{10}$ (Co $Q_{10}$) was administered intraperitoneally to each rat, and the EEG patterns were recorded in the same way as above. As a control, a solvent alone was administered intraperitoneally to control rats at the same rate.

(2) Results

Figure 1:
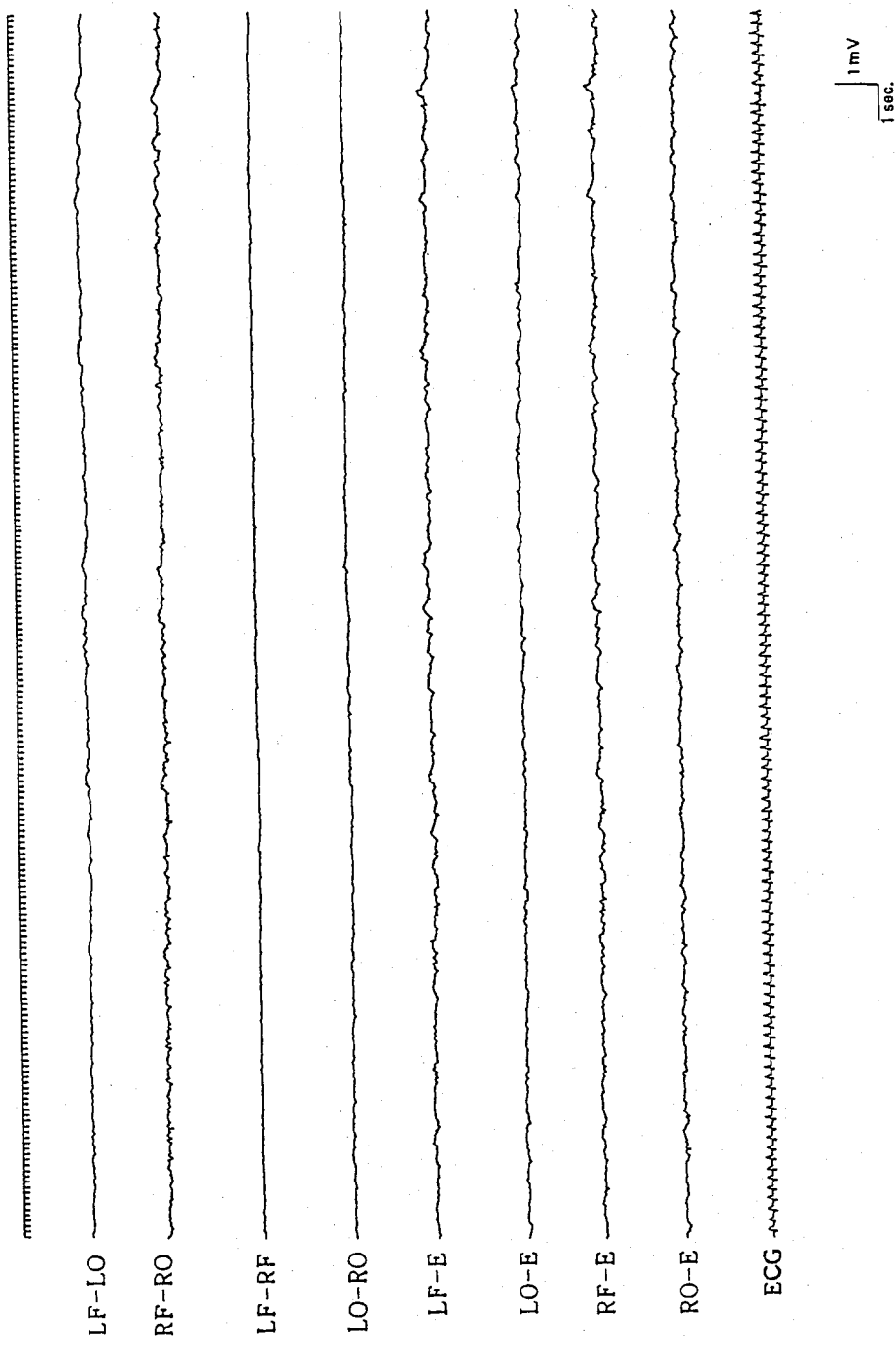
FIGS. 1 to 5 show electroencephalograms (EEG) and electrocardiograms (ECG) taken at different times during the tests described in Experimental Example 1 below.
Figure 2:
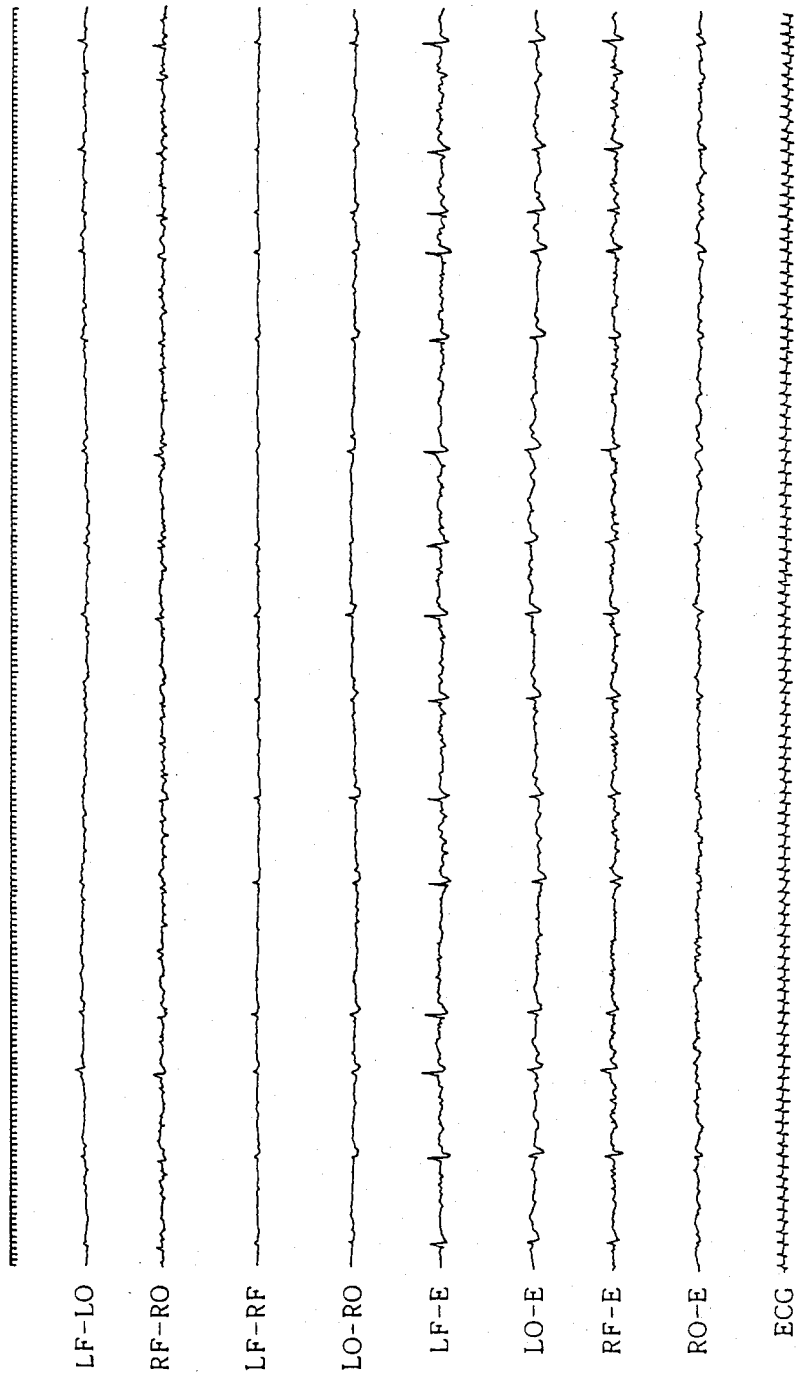
Figure 3:
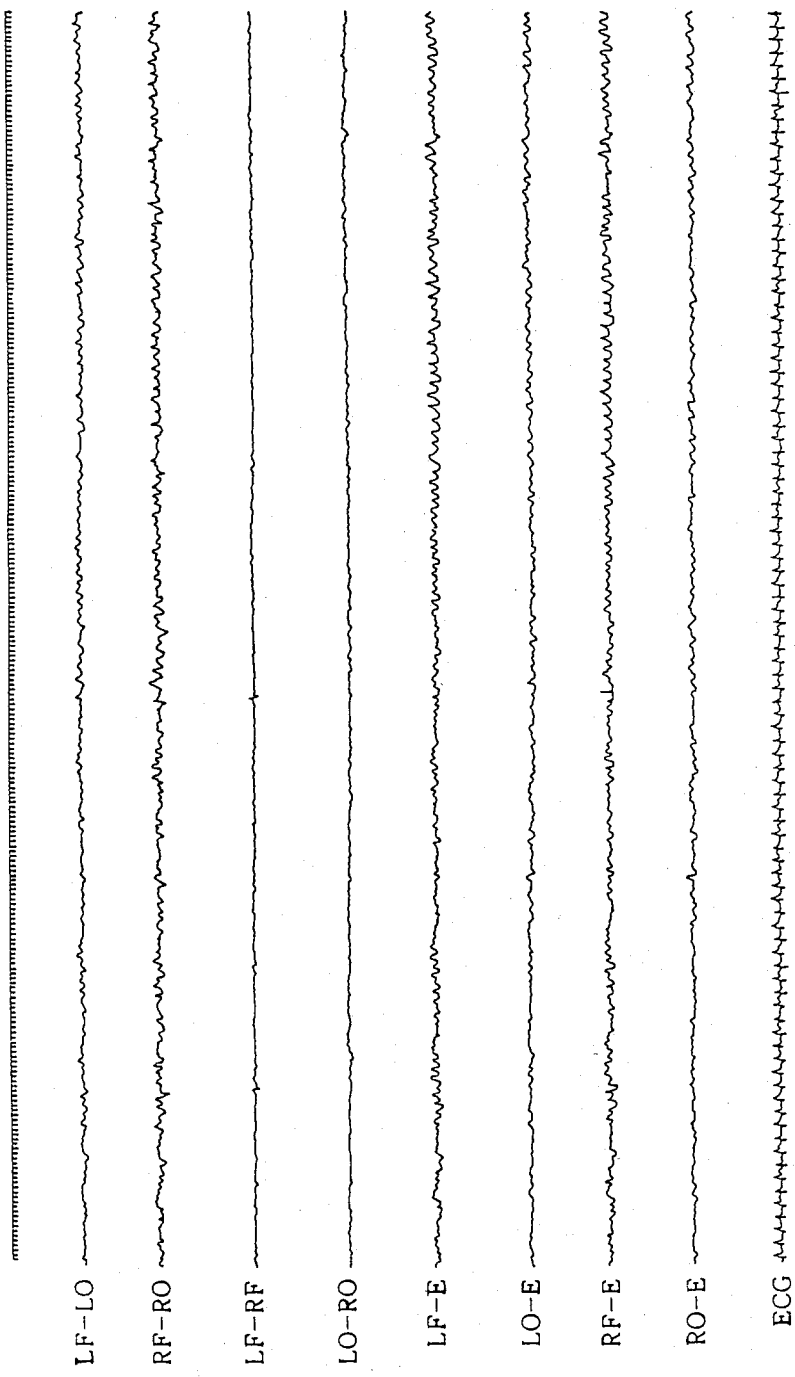
Figure 4:
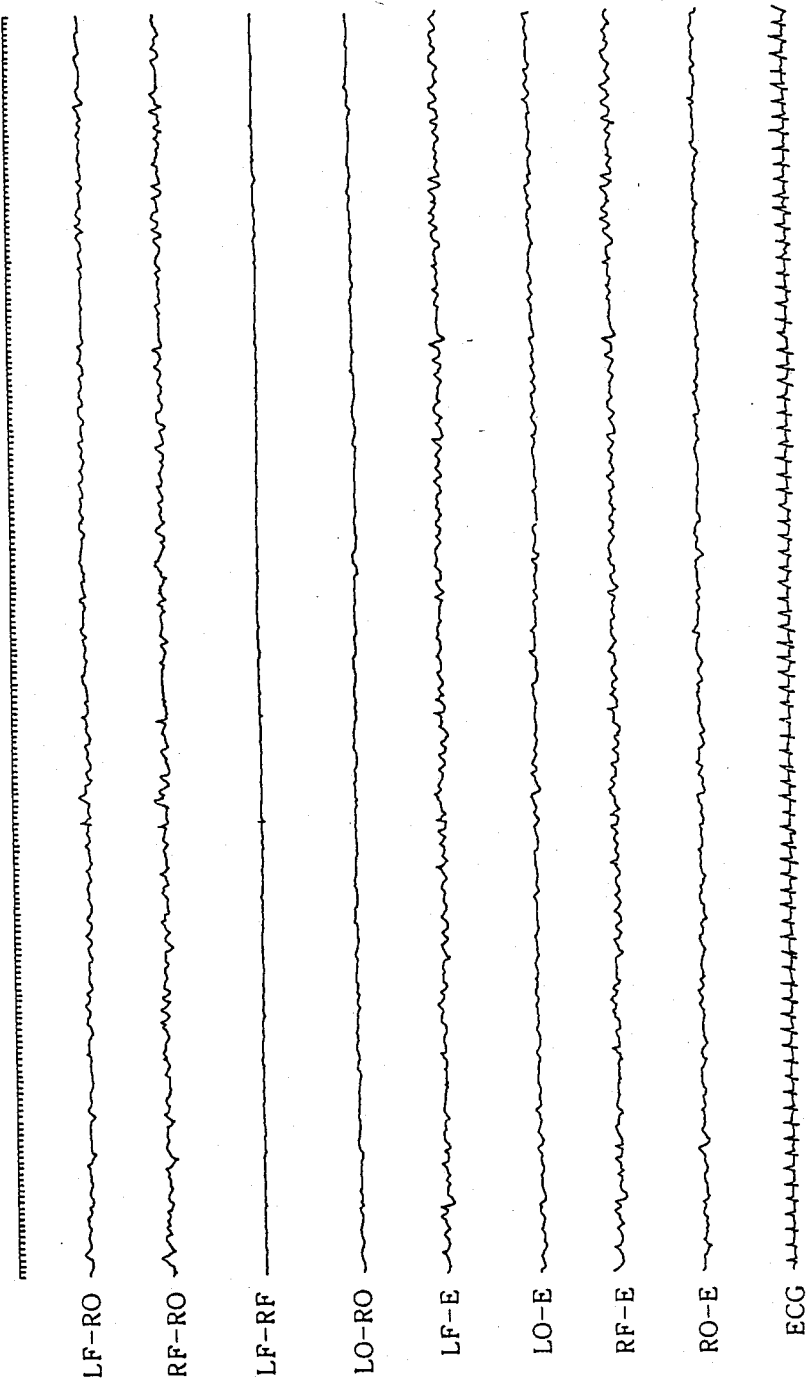
Figure 5:
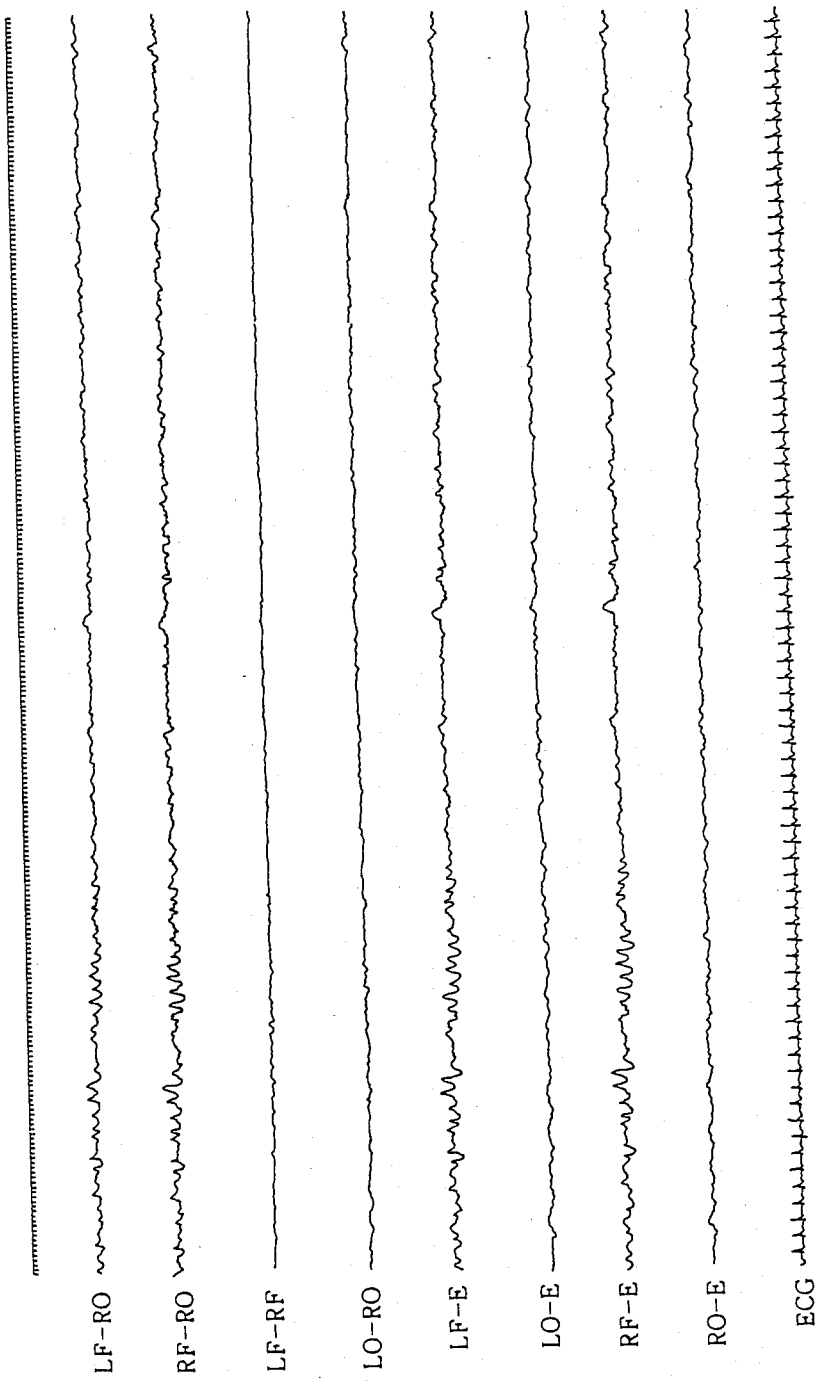

The electroencephalogram (EEG) and electrocardiogram recordings are shown in FIGS. 1 to 5. FIG. 1 shows an EEG taken one minute before the administration of penicillin G, FIG. 2 shows an EEG taken 20 minutes after the administration of penicillin G, FIG. 3 shows an EEG taken 10 minutes after the administration of Co $Q_{10}$, FIG. 4 shows an EEG taken 60 minutes after the administration of Co $Q_{10}$, and FIG. 5 shows an EEG taken 200 minutes after the administration of Co $Q_{10}$.

It is evident from the results of FIGS. 1 to 5 that the spike discharge disappears about 10 minutes after the administration of coenzyme $Q_{10}$, one of the compounds used in this invention, and disappearance of the spike discharge lasts for more than 200 minutes.

Further experiments were conducted by the same procedure as used in Experimental Example 1, except that the time of the administration of coenzyme $Q_{10}$ was changed. The results are shown in Table 1 below as Experimental Examples 2 to 4. In Table 1, PCG represents penicillin G.

TABLE 1

| Experimental Example | Results |
|---|---|
| | When 100 mg/kg of Co $Q_{10}$ was administered 107 minutes after applying PCG, the spike discharge disappeared 20 minutes thereafter and the disappearance lasted for more than 120 minutes. |
| | When 100 mg/kg of Co $Q_{10}$ was administered 65 minutes after applying PCG, the spike discharge disappeared 19 minutes thereafter and the disappearance lasted for more than 60 minutes. |
| 4 | Unlike Experimental Examples 1 to 3, 100 mg/kg of Co $Q_{10}$ was first administered, and then PCG was applied 64 minutes thereafter. In this case, no spike discharge occurred for more than 80 minutes. |

The results of Experimental Examples 1 to 4 indicate that coenzyme $Q_{10}$ can be used for the treatment and prevention of central seizures, especially seizures associated with epilepsy.

The results of toxicity tests on coenzyme $Q_{10}$ used in this invention are shown below.

1. Acute toxicity

Table 2 shows acute dosages in mg/kg.

TABLE 2

| | Method of administration | | | |
|---|---|---|---|---|
| | Oral | Intramuscular | Subcutaneous | Intravous |
| Rat | 4,000 | 500 | 500 | 250 |
| Mouse | 4,000 | 500 | 500 | 250 |

2. Chronic toxicity

Coenzyme $Q_{10}$ was forcibly administered per os to both male and female Wistar rats at doses of 6, 60 and 600 mg/kg/day for a period of 26 successive weeks. After this testing period, an examination of the general condition, a blood test, a urine test and a morphological observation (macroscopic and histologic) were conducted. No differences at all from the control group were observed.

As will be appreciated from the above results, the coenzymes Q used in this invention can be used as a pharmaceutical substance for treatment of spasms with an extremely high saftey, and can be administered in successive doses for a long period of time as a remedial and prophylactic medicine for treating epilepsy. The therapeutically effective dosage of these coenzymes Q varies depending on the type and the degree of spasm, but is usually about 10 to 1,000 mg, preferably about 20 to 500 mg, per day for an adult human being.

For the administration of coenzyme Q in this invention, suitable dosage forms include powders, tablets, granules, capsules, injections, suppositories, or buccal tablets. These preparations can be produced by known methods using conventional excipients.

In preparing a powder, for instance, the substance of this invention is adsorbed on an excipient such as magnesium carbonate, silicic anhydride, synthetic aluminosilicate, calcium phosphate, lactose, starch, microcrystalline cellulose, dextrose, or hydroxypropylcellulose. Tablets or capsules can be produced by properly treating the powder obtained in the above manner.

Injections can be prepared by forming an aqueous solution of the substance of this invention with a nonionic surfactant in the conventional way. As the nonionic surfactant, a hydrogenated castor oil-ethylene oxide adduct (such as Nikkol HCO), a sorbitan fatty acid ester-ethylene oxide adduct (such as Tween), an alkylphenol-ethylene oxide adduct, a sorbitan fatty acid ester (such as Span), and the like may be employed. A common adjuvant such as propylene glycol or dextrose may be added to the composition.

Examples of actual formulations of dosage forms according to this invention are described below. The present invention is not limited to these examples.

| Formulation Example 1: Capsules | |
|---|---|
| Coenzyme $Q_{10}$ | 5 g |
| Microcrystalline cellulose | 80 g |
| Corn starch | 20 g |
| Lactose | 22 g |
| Polyvinylpyrrolidone | 3 g |
| Total amount | 130 g |

The above composition was granulated by a conventional method and filled into hard gelatin capsules.

| Formulation Example 2: Powder | |
|---|---|
| Coenzyme $Q_{10}$ | 50 g |
| Microcrystalline cellulose | 400 g |
| Corn starch | 550 g |
| Total amount | 1,000 g |

Coenzyme $Q_{10}$ was dissolved in acetone, and the solution was adsorbed in microcrystalline cellulose and dried. The resulting material was mixed with corn starch and worked into a powder by a conventional method.

| Formulation Example 3: Tablets | |
|---|---|
| Coenzyme $Q_{10}$ | 5 g |
| Corn starch | 10 g |
| Refined white sugar | 20 g |
| Calcium carboxymethylcellulose | 10 g |
| Microcrystalline cellulose (Avicel) | 40 g |
| Polyvinylpyrrolidone (K-30) | 5 g |
| Talc | 10 g |
| Total amount | 100 g |

Coenzyme $Q_{10}$ was dissolved in acetone and the solution was adsorbed on microcrystalline cellulose and dried. The resulting material was mixed with corn starch, refined white sugar and calcium carboxymethylcellulose, then with an aqueous solution of polyvinylpyrrolidone as a binder, and then granulated. The granulated material was mixed with talc as a lubricant, and was then mixed further and worked into tablets each weighing 100 mg.

| Formulation Example 4: Injection | |
|---|---|
| Coenzyme $Q_{10}$ | 10 g |
| Nikkol HCO-60 | 37 g |
| Sesame oil | 2 g |
| Sodium chloride | 9 g |
| Propylene glycol | 40 g |
| Phosphate buffer (0.1 M, pH 6.0) | 100 ml |
| Total amount (after being diluted with distilled water) | 1,000 ml |

Coenzyme $Q_{10}$, Nikkol HCO-60, sesame oil and half of the propylene glycol were mixed and heated to about 80° C. to form a solution. The phosphate buffer and the distilled water, in which the sodium chloride and the remaining propylene glycol were dissolved, were heated to about 80° C. and added to this solution, thereby preparing an aqueous solution in a total amount of 1,000 ml. This aqueous solution was pipetted into 1-ml ampules. These ampules were closed by melting and heat-sterilized.

Formulation Example 5

Capsules were produced in the same way as in Formulation Example 1 except that coenzyme $Q_6$ was used in place of coenzyme $Q_{10}$.

Formulation Example 6

An injection was produced in the same way as in Formulation Example 4 except that coenzyme $Q_7$ was used in place of coenzyme $Q_{10}$.

The embodiments of the invention in which an exclusive property or privilege is claimed are defined as follows:

1. A method for the treatment of seizures which comprises administering to a subject suffering from seizures a therapeutically effective amount of a composition comprising a coenzyme Q of the formula:

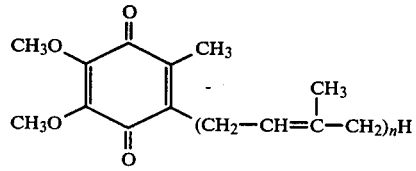

wherein n is an integer of from 7 to 10, in combination with a pharmaceutically acceptable carrier.

2. A method as claimed in claim 1, wherein n is 10.

3. A method as claimed in claim 1, wherein said subject is a human being, and said coenzyme Q is administered in a dosage in the range of 10 to 1,000 mg per day.

4. A method as claimed in claim 3, wherein said dosage is 20 to 500 mg per day.

5. A method for treating epilepsy which comprises administering to a subject suffering from epilepsy a therapeutically effective amount of a composition comprising a coenzyme Q of the formula:

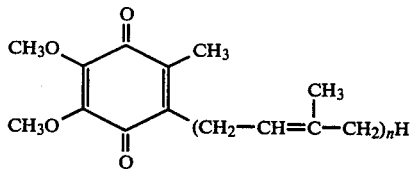

wherein n is an integer of from 7 to 10, in combination with a pharmaceutically acceptable carrier.

* * * * *